United States Patent [19]

Gordon

[11] Patent Number: 5,184,719
[45] Date of Patent: Feb. 9, 1993

[54] TAMPER RESISTANT, DISPOSABLE TOOTHBRUSH AND FLOSSING DEVICE

[76] Inventor: Chester D. Gordon, 19023 Galway Ave., Carson, Calif. 90746

[21] Appl. No.: 906,434

[22] Filed: Jun. 30, 1992

[51] Int. Cl.⁵ .............................................. B65D 81/20
[52] U.S. Cl. .............................. 206/209.1; 15/104.94; 132/309; 132/323; 206/362.3
[58] Field of Search ............... 15/104.93, 104.94, 184; 132/309, 323–328; 206/209.1, 63.5, 362.1–362.4, 581, 823

[56] References Cited

U.S. PATENT DOCUMENTS

| | | |
|---|---|---|
| 615,357 | 12/1898 | Johnson et al. ............... 206/362.3 |
| 1,488,214 | 3/1924 | Mason .................................. 132/309 |
| 1,904,609 | 4/1933 | Bleadon .......................... 206/209.1 |
| 4,198,171 | 4/1980 | Lampka et al. ................ 206/362.2 |
| 4,436,203 | 3/1984 | Reyner ................................... 206/807 |
| 4,530,129 | 7/1985 | Labick et al. .................... 206/362.3 |
| 4,880,111 | 11/1989 | Bagwell et al. ................. 206/209.1 |
| 5,044,386 | 9/1991 | Nelson ................................. 132/324 |
| 5,067,503 | 11/1991 | Stile ................................... 206/63.5 |
| 5,097,852 | 3/1992 | Wu ....................................... 132/328 |
| 5,139,142 | 8/1992 | Simon .............................. 206/362.4 |

Primary Examiner—Jimmy G. Foster
Attorney, Agent, or Firm—Willie Krawitz

[57] ABSTRACT

A three-component, tamper resistant, toothbrush comprises a brush and flossing device connected by a handle portion which is sufficiently flexible to allow the brush to be bent back and contact the flossing device without excessive force being applied by the user. The brush is covered by a dry or wet dentifrice, or a dentifrice-water paste. A thin plastic cover surrounds and seals the brush and provides a vacuum seal which maintains sterility and allows the brush to be precoated with dentifrice and retain the pre-moistened dentifrice within the cover. The flossing device comprises forklike prongs between which is mounted a free span of floss under tension. A socket attachment may be provided so that additional implements such as stimulators, plaque removers, etc., can be connected to the device for use in a convenient manner. If desired, the handle can be bent back to enable the dentifrice-coated brush to contact the floss and apply some of the dentifrice thereto.

8 Claims, 1 Drawing Sheet

U.S. Patent      Feb. 9, 1993      5,184,719
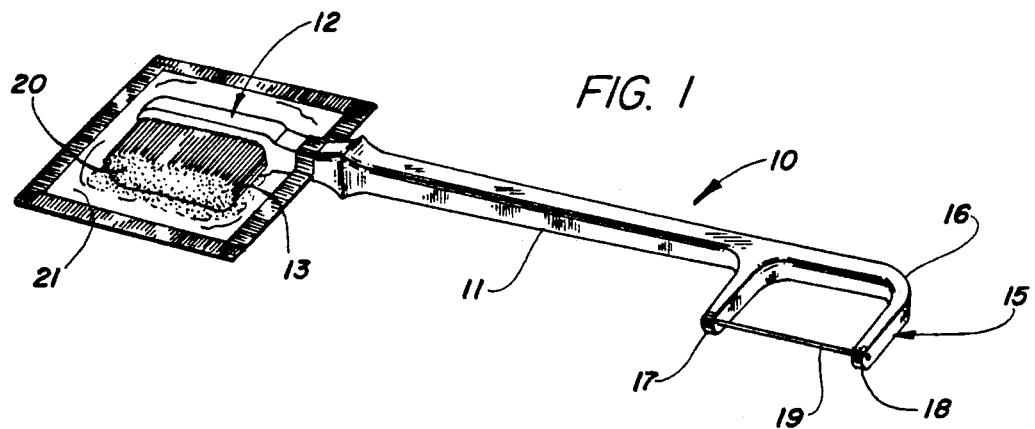
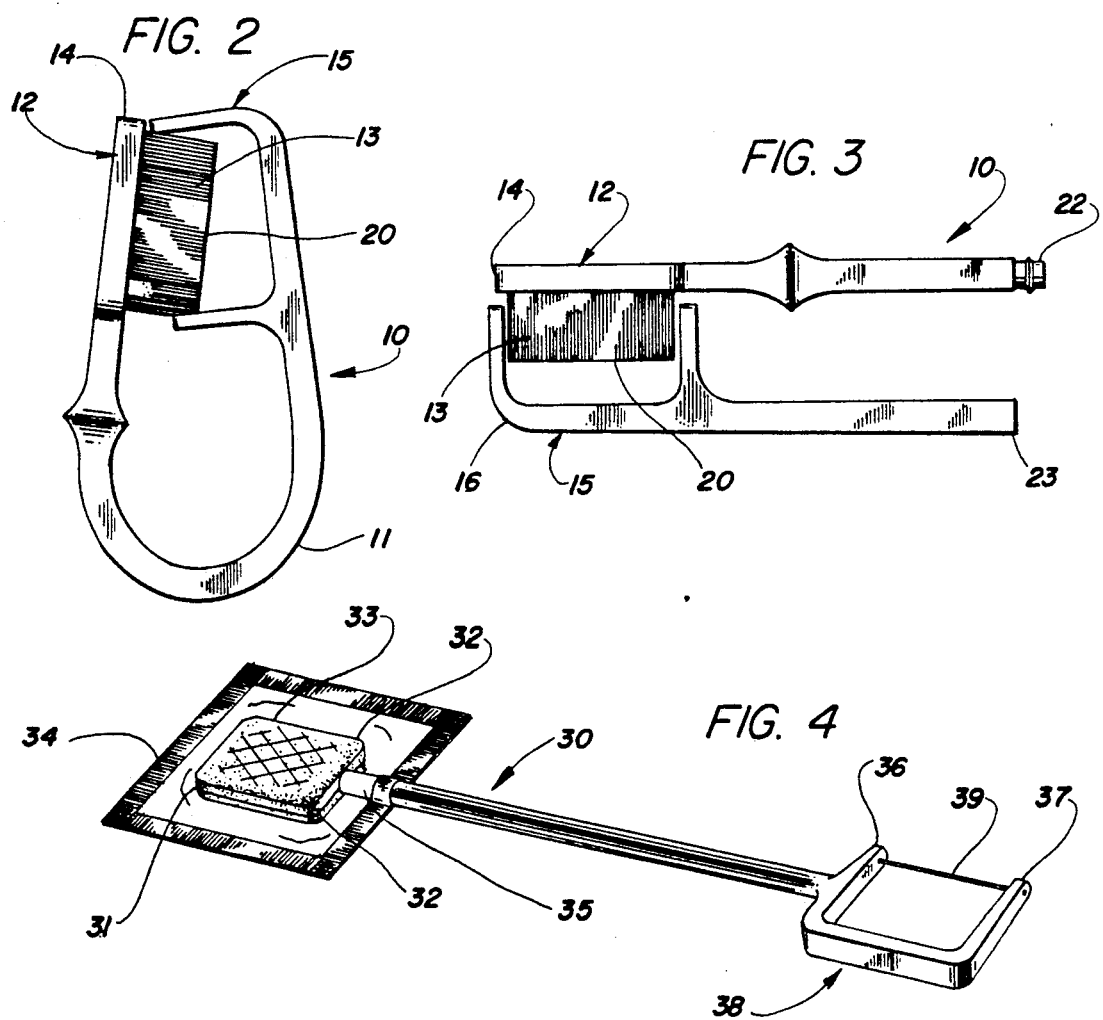

TAMPER RESISTANT, DISPOSABLE TOOTHBRUSH AND FLOSSING DEVICE

BACKGROUND OF THE INVENTION

This invention relates to a new and improved tamper resistant, disposable toothbrush and flossing device packaged in an inexpensive, compact, and easy to use unit. The toothbrush is designed to provide a simplified and convenient means of flossing and brushing the user's teeth with only one hand. The toothbrush and flossing device may be manually separated for discrete and compact storage and also can be manually bent backward to contact the floss with the dentifrice coated brush. The ability to coat the floss with dentifrice enables fluoride in the dentifrice to be applied between the teeth while reducing or eliminating the need for having both waxed and unwaxed floss, and the problems associated with wax buildup in the case of waxed floss.

Various disposable tooth cleaning devices for reducing the incidence of dental and periodontal disease are known, and typical prior art devices are shown in U.S. Pat. Nos. 3,165,776; 4,503,871; 4,522,524; 4,530,129; 4,588,089; 4,865,481; and, 4,966,176. None of these prior art devices provide a toothbrush and flossing device where the flossing portion can be coated with dentifrice, or the like, and which do not require a separate source of dentifrice.

Also, none of these prior art devices provide a sterile packaging around the bristle section of the tooth cleaning device in association with a dentifrice. Moreover, none of these cleaning devices can be separated into two components for providing compact and discrete storage, making possible the transfer of dentifrice paste, moist or dry, from the toothbrush to the floss section, and allowing other dental attachments to be attached to the toothbrush. Consequently, a need exists for comprehensive and disposable dental hygienic care that is sterile, portable, inexpensive and readily available for use.

Preferably, a number of such devices should be available in one package in order to reduce the frequency of purchase. Also, it would be helpful if the package surrounding the moist dentifrice coated portion of the device was tamper resistant and easily separable from the device.

THE INVENTION

According to the invention, a disposable toothbrush and flossing device is provided for maintaining dental hygienic care when time and location constraints or added tasks prohibit or make inconvenient the use of traditional toothbrushes, toothbrush or dentifrice containers, floss containers or the use of both hands.

The disposable toothbrush and flossing device comprises a flexible, three-component dental hygienic care unit, one component being a flexible and longitudinally elongated plastic handle portion. The handle should be sufficiently flexible to allow the dentifrice coated brush to come in contact with the floss without excessive force being applied by the user. An optional socket attachment may be provided on the handle so than an additional implement such as a stimulator, mirror, plaque remover, etc. can be suitably connected to the device for use in a conventional manner.

The second component of the disposable toothbrush and flossing device is a brush portion of suitable shape, similar to the usual toothbrush. The brush portion comprises a plurality of bristles constructed typically of nylon, acrylic, polyester, etc., and blends of these materials. A dry or wet dentifrice paste covers the brush and they are protected from handling, dust, bacteria, etc., by a vacuum seal in by a thin plastic cover.

The third component of the disposable toothbrush is a flossing device comprising a forklike portion mounted on the side opposite the brush component. The forklike portion provides a suitable space between which is mounted a free span of floss under constant tension.

BRIEF DESCRIPTION OF THE DRAWINGS

FIG. 1 is a perspective view of the disposable toothbrush of this invention illustrating the pre-packaged brush portion and accompanying flossing tool;

FIG. 2 is an external view in side elevation view of the disposable toothbrush, showing the brush portion in contact with the floss; and, FIG. 3 is an external view in side elevation of the disposable toothbrush, showing the brush and floss sections as separate components; and, FIG. 4 is a perspective view of a modification of the disposable toothbrush and accompanying flossing tool.

DESCRIPTION OF THE PREFERRED EMBODIMENTS

The disposable toothbrush 10 of this invention is shown in FIGS. 1, 2, 3 and 4, and comprises a generally longitudinally elongated plastic handle portion 11 of mostly constant width whose diameter is sufficiently wide to be easily grasped by the hand, and small enough to minimize material and storage space, and is generally rectangular in cross section. A brush element 12 having a plurality of bristles 13 is mounted at one end 14 of the handle portion, and a floss portion 15 is mounted at the opposite end 16 of the handle. The floss portion comprises twin fork elements 17 and 18, and a flossing thread 19 mounted therebetween.

A wet dentifrice, or dentifrice-water material 20 is shown coating the bristles 13, and the entire end 14 of the handle portion 11 is vacuum sealed in a suitable package 21.

The handle portion 11 of the device is shown in FIG. 2 as being bent inwardly, without requiring excessive force, to allow the dentifrice coated bristles 13 to contact and coat the flossing thread 19. The ability to coat the flossing thread 19 with a dentifrice-water paste 20 either by bending the toothbrush and contacting the floss portion 15, or by separating the device into two parts as shown in FIG. 3, not only allows the floss 19 to become lubricated, but also facilitates fluoride penetration between the teeth. Also, the option of orienting the brush element 12 on a plane that is perpendicular to the twin fork elements 17 and 18 of the flossing portion 15 would allow the floss 19 to become lubricated. Moreover, the option of adding the wet dentifrice paste 20 eliminates the need for having both waxed and unwaxed floss, and the problems associated with wax buildup when using waxed floss.

As shown in FIG. 3, another embodiment of this invention provides an optional socket attachment 22 having a generally tubular shape to connect an additional implement such as a stimulator, mirror, plaque remover, etc., to the toothbrush for use in a conventional manner. Also, the separation of the brush element 12 and the flossing portion 15 at its center 23 allows for a compact and discrete storage and an additional means for coating the flossing thread 19 with a dry or wet dentifrice, or a dentifrice-water paste 20.

Another embodiment of the brush element 12 of the device is shown in FIG. 4, and consists of a thin, generally rectangular shaped plastic portion 31 sandwiched between a pair of dense and durable sponge like surfaces 32. The dense sponge surfaces 32 serve to evenly disperse the wet dentifrice material 33 across the surface of the teeth while providing sufficient roughage to quickly and safely remove plaque and food particles from the tooth surfaces and gum line.

A suitable package 34 surrounds the end of the handle portion 35 and the sponge surfaces 32 to produce a bacteria free vacuum seal. The handle portion 35 of the disposable toothbrush 30 can bend inwardly towards the twin fork elements 36 and 37 of the flossing portion. This allows the dentifrice coated sponge surface 32 to contact and coat the flossing thread 39 with a dentifrice-water paste.

Typically, the handle portion 11 is about $2\frac{1}{2}''$–$3\frac{1}{2}''$ long, $\frac{1}{4}''$ in width, and $3/32''$–$\frac{1}{8}''$ thick; brush element 12 is about $\frac{1}{4}''$–$\frac{1}{2}''$ wide, and $\frac{3}{4}''$–$1\frac{1}{4}''$ long; sponge surface 32 is about $\frac{1}{2}''$ in width, $\frac{1}{4}''$ long, and $1/16''$ thick; the distance between the fork elements 17 and 18, which determines the length of the flossing thread 19, is about $\frac{3}{8}''$–$\frac{3}{4}''$ wide; and, the fork elements themselves are about $\frac{1}{2}''$–$\frac{3}{4}''$ long.

Overall, the disposable toothbrush and flossing portion provides a simplified and convenient means of flossing and brushing, and encourages the performance of proper oral hygienic care, thereby reducing the risk of periodontal problems and disease.

I claim:

1. A three-component tamper resistant disposable toothbrush comprising:
   a. a handle portion;
   b. a bristle portion defining an attachment surface, and a free surface, the attachment surface being imbedded within the handle portion, the bristle portion being coated with a dentifrice paste;
   c. a flossing element portion; and,
   d. a vacuum sealed plastic cover surrounding the bristle portion, thereby maintaining the dentifrice moist and inhibiting bacteria buildup.

2. The toothbrush of claim 1, in which the bristle portion comprises a plurality of bristles which are soft flexible materials selected from the class consisting of nylon, acrylic, polyester, and blends of these materials.

3. The toothbrush of claim 1, in which the plastic cover is a flexible housing selected from the class consisting of nylon, acrylic, polycarbonate, and polypropylene.

4. The toothbrush of claim 1 comprising a socket attachment about the middle of the elongated portion for attaching a dental implement thereto, including a stimulator, mirror, and plaque remover.

5. The toothbrush of claim 1, in which the floss can be coated with the dentifrice paste by bending the handle portion to contact the flossing element with the dentifrice coated bristles.

6. The toothbrush of claim 1, in which the floss can be coated with the dentifrice paste by separating the toothbrush into two parts and connecting their respective ends so as to allow the floss to become lubricated.

7. The toothbrush of claim 1, in which the handle portion dimensions are about $2\frac{1}{2}''$–$3\frac{1}{2}''$ long, $\frac{1}{4}''$ in width, and $3/32''$–$\frac{1}{8}''$ thick, the brush element is about $\frac{1}{4}''$–$\frac{1}{2}''$ wide, and $\frac{3}{4}''$–$1\frac{1}{4}''$ in length, the sponge surface is about $\frac{1}{2}''$ in width, $\frac{1}{4}''$ long, and $1/16''$ thick, and the distance between the fork elements is about $\frac{3}{8}''$–$\frac{3}{4}''$ wide and $\frac{1}{2}''$–$\frac{3}{4}''$ in length.

8. A tamper resistant, disposable toothbrush, comprising:
   a. a handle portion;
   b. a bristle portion being attached to the handle portion, and a free gripping surface forming a part of the handle portion, the bristle portion bearing a dentifrice which is dry or wet, or a paste; and,
   c. a vacuum sealed plastic cover surrounding the bristle portion, thereby maintaining the dentifrice, or the paste in its original condition and free from extraneous material, and inhibiting bacteria buildup.

* * * * *